United States Patent [19]

O'Lenick, Jr.

[11] Patent Number: 5,770,751

[45] Date of Patent: Jun. 23, 1998

[54] MEADOWFOAM SULFOSUCCINATES

[75] Inventor: Anthony J. O'Lenick, Jr., Lilburn, Ga.

[73] Assignee: Fan Tech Ltd., Chicago, Ill.

[21] Appl. No.: 767,475

[22] Filed: Dec. 16, 1996

Related U.S. Application Data

[63] Continuation-in-part of Ser. No. 692,376, Jul. 31, 1996, which is a continuation-in-part of Ser. No. 516,138, Aug. 17, 1995.

[51] Int. Cl.$^6$ .................................................. C07C 233/00
[52] U.S. Cl. .............................. 554/49; 554/50; 554/401; 554/64
[58] Field of Search ................................. 554/49, 50, 61, 554/64

[56] References Cited

U.S. PATENT DOCUMENTS 4,490,355  12/1984  Desai ........................................ 424/70

*Primary Examiner*—Gary Geist
*Assistant Examiner*—Deborah D. Carr

[57] ABSTRACT

The present invention deals with the certain novel meadowfoam derived sulfosuccinates. These materials are useful as cosmetic ingredients as additives to shampoo systems where outstanding liquidity, resistance to oxidation, and minimal odor variation are required.

10 Claims, No Drawings

MEADOWFOAM SULFOSUCCINATES

RELATED APPLICATIONS

This application is a continuation in part of copending application Ser. No. 692,376, filed: Jul.31, 1996 which is in turn a continuation in part of copending application Ser. No. 516,138 filed Aug. 17, 1995.

BACKGROUND OF THE INVENTION

1. Field of the Invention

The present invention deals with the certain novel sulfosuccinates which are prepared by the reaction of a meadowfoam based alkanolamide, maleic anhydride and sodium sulfite. These materials are extremely mild, have essentially no odor and therefore are useful as cosmetic ingredients. These materials have outstanding liquidity, resistance to oxidation, and minimal odor variation are required. This combination of properties make these compounds excellent candidates as additives to personal care products like shampoos where they thicken formulations and stabilize foam.

2. Description of the Art Practices

Alkanolamides perform a variety of functions including viscosity enhancement, foam stabilization, emulsification, and detergency. Chemically, alkanolamides are the reaction product of an alkanolamine and a fatty material. Fatty materials are a class of compounds which include fatty carboxylic acids, fatty methyl esters and fatty glycerides (also called oils). The source of the fatty materials include coconut, peanut, soybean, and rapeseed oils, fractionated and non-fractionated fatty methyl esters and acids of almost any carbon length.

Variation of carbon chain lengths in the fatty source has direct effect upon alkanolamide properties. While short chain fatty materials result in compounds useful as humectants and hair anti-tangle agents, products based upon 8 to 10 carbon fatty acids exhibit foam stability but contribute little as thickeners. The medium range 12 to 14 carbon fatty acids are the best foam boosters, while also showing good viscosity building properties. Lauric-myristic diethanolamides are common ingredients in formulations of high foaming products such as dish wash detergent, bubble bath, and hair shampoo. They also contribute emollient and conditioning effects upon skin and hair in many formulations. This is why the lauric myristic alkanolamides have become the workhorse of the cosmetic industry.

The use of higher molecular weight unsaturated fatty alkanolamides reduce foam and foam stabilization but give good viscosity build. The optimum performance in a formulation is often obtained when one employs blends of alkanolamides having differing carbon chain lengths. This can result in the desired properties of both materials. Oleic and linoleic alkanolamides are excellent viscosity builders at low concentration in most shampoos and are of particular interest in formulations that contain surfactants which are difficult to thicken. These higher molecular weight unsaturated products because of their unsaturation suffer from oxidative instability and interfere with the fragrance of many products.

The recent availability of meadowfoam oil, with it's 20 to 22 carbon atoms and the specific location of it's double bonds, and it's reaction to make alkanolamides results in the preparation liquid stable alkanolamides, acceptable for use in personal care applications.

The selection of a mono-hydroxy alkanolamide as a raw material used to make sulfosuccinates useful in hair and skin care applications. The sulfosuccinates of the present invention have outstanding skin feel.

None of the prior sulfosuccinates possess the critical meadowfoam moiety. Molecules of the current invention have the meadowfoam alkyl group in the alkanolamide, which is subsequentiy converted into the sulfosuccinate by the technology which will become apparent by the disclosure of the present application.

THE INVENTION

This invention relates to a particular group of sulfosuccinates made by the reaction of a meadowfoam oil, meadowfoam based alkanolamide. The meadowfoam alkanolamide is the subject of the copending application from which this application is a continuation in part. The terms meadowfoam oil, fatty acid or methyl ester as used herein refer to a specific alkyl distribution of the groups which is are native to a plant Limnathes Alba, commonly called meadowfoam oil. Meadowfoam oil is harvested from a plant and sold commercially by The Fanning Corporation under the tradename "Fancor Meadowfoam".

The unique structure of the oil coupled with the proper selection of the alkanolanolamide chosen to make the sulfosuccinate results in a liquid sulfosuccinate with oxidative stability and skin feel heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Additional aspects of the invention is the application of these materials as personal care applications were the specific properties of the sulfosuccinate having the unique distribution of the meadowfoam on the other result in superior liquidity, lubricity, and outstanding oxidative stability.

The compounds of the current invention are sulfosuccinates derived from meadowfoam conforming to the following structure;

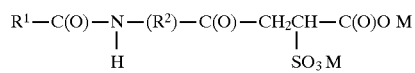

$R^1$ is derived from meadowfoam and specifically is

60–65% by weight

12–20% by weight a mixture of

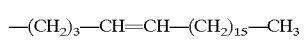

and

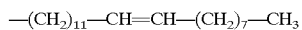

and

15–28% by weight $-(CH_2)_3-CH=CH-(CH_2)_6-CH=CH-(CH_2)_6-CH_3;$ $R^2$ is:

$-(CH_2CH_2-O)_x-(CH_2CH(CH_3)O)_y-$ x, and y are independently 0 or 1 with the proviso that x+ y is greater than 0;

M is a cation selected from K or Na.

It is also envisioned that the compounds of the present invention can be blended with other sulfosuccinates to obtain products which will have improved liquidity and improved viscosity build in formulations are well as enhanced foam stabilization effects.

The invention also teaches that a sulfosuccinate can be made by the following sequence of reactions:

Reaction 1

Alkanolamide + Maleic Anhydride $R^1(O)C-N-(CH_2CH_2-O)_x-(CH_2CH(CH_3)O)_y-H$ + Maleic Anhydride (structure shown)
        |
        H
        Meadowfoam Alkanolamide $R^1(O)C-N-(CH_2CH_2-O)_x-(CH_2CH(CH_3)O)_y-C(O)-CH=CH-C(O)-OH$
        |
        H
        Meadowfoam Maleate Half Ester x, and y are independently 0 or 1 with the proviso that x+ y is greater than 0.

Reaction 2

$R^1(O)C-N-(CH_2CH_2-O)_x-(CH_2CH(CH_3)O)_y-C(O)-CH=CH-C(O)-OH$
        |
        H

+ $Na_2SO_3$ (in water)

$R^1(O)C-N-(CH_2CH_2-O)_x-(CH_2CH(CH_3)O)_y-C(O)-CH2-CH-C(O)-O\,Na$
        |                                              |
        H                                              $SO_3Na$

Another aspect of the present invention is the intermediate meadowfoam maleate conforming to the following structure:

$R^1(O)C-N(H)-(R^2)-C(O)-CH=CH-C(O)-OH$ $R^1$ is derived from meadowfoam and is;

60–65% by weight $-(CH_2)_3-CH=CH-(CH_2)_{13-CH3}$

12–20% by weight a mixture of $-(CH_2)_3-CH=CH-(CH_2)_{15}-CH_3$ and $-(CH_2)_{11}-CH=CH-(CH_2)_7-CH_3$ and 15–28% by weight $-(CH_2)_3-CH=CH-(CH_2)_6-CH=CH-(CH_2)_6-CH_3;$ $R^2$ is $-(CH_2CH_2-O)_x-(CH_2CH(CH_3)O)_y-;$ x, and y are independently 0 or 1 with the proviso that x+ y is greater than 0.

In addition to being an intermediate in the preparation of the sulfosuccinates of the present invention this maleate in aqueous solution neutralized to pH of 7 is a good anionic surfactant.

Preferred Embodiment

In a preferred embodiment M is K.
In a preferred embodiment M is Na.
In a preferred embodiment x is 1, and y is 0.
In a preferred embodiment x is 0, and y is 1.
In a preferred embodiment x is 1, and y is 1.

EXAMPLES

RAW MATERIALS

Meadowfoam Oil

Meadowfoam Oil can be used as a triglyceride, which is the oil as provided, reacted with methanol in processes known to those skilled in the art to make methyl ester, or reacted using technology known in the art to make carboxylic acids. The CAS number of meadowfoam oil is 153065-40-8. The methyl ester of meadowfoam is the preferred statring material.

Alkanolamines

The alkanolamides useful in the present invention have one hydroxyl group present. They conform to the following structure:

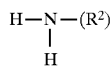

$R^2$ is:

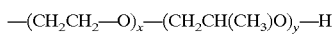

x, and y are independentiy 0 or 1 with the proviso that x+ y is greater than 0.

Class 1 (monoalkanolamines)

Monoalkanolamines are products of commerce and are available commercially from many companies like Union Carbide. $R^3$ is H in this class of compounds.

| Example | | $R^2$ | |
|---|---|---|---|
| | | x | y |
| 1 | Monoethanolamine | 1 | 0 |
| 2 | Monoisopropanolamine | 0 | 1 |
| 3 | Mixed Amine 1 | 1 | 1 |
| 4 | Mixed Amine 2 | 10 | 10 |

Amide Synthesis

The amidification reaction is carried out using an excess of alkanolamine or meadowfoam or more typically using an equivalent of each. The reaction can be carried out with or without catalyst.

General Procedure—Meadowfoam Methyl Ester

To the specified number of grams of alkanolamine (examples 1–6) is added then 354.0 grams of the meadowfoam methyl Ester. The temperature of the mass is raised to 150°–200° C. The amine value drops to vanishingly small levels.

The products are clear liquids and are liquid to extraordinary temperatures. They are used to make sulfosuccinates.

| Example | Alkanolamine Example | Grams |
|---|---|---|
| 5 | 1 | 60.0 |
| 6 | 2 | 75.0 |
| 7 | 3 | 118.0 |
| 8 | 4 | 1045.0 |

Maleate Synthesis

The alkanolamide examples 5, 6 and 7 are used as intermediates in the synthesis of maleate ester which is in turn sulfonated in a latter step. The reaction sequence is as follows:

The Amide from part 1 is added to a suitable vessel. It is heated to 60° C. or until molten. Next the maleic anhydride is added slowly, keeping the temperature between 60° and 80° C. The temperature is held for 2–3 hours. The acid value is checked and when 97% of the reaction has occurred, the material is cooled. The material is ready for use without further processing.

| Example Number | Amide Derivative | | Maleic Anhydride |
|---|---|---|---|
| | Example | Grams | Grams |
| 9 | 5 | 386.0 | 98.0 |
| 10 | 6 | 401.0 | 98.0 |
| 11 | 7 | 444.0 | 98.0 |
| 12 | 8 | 1371.0 | 98.0 |

Sulfonation of the Maleate

The maleate is sulfonated in aqueous solution as follows:

To the specified amount of water is added the sulfite. Most commonly sodium sulfite is used, but potassium sulfite may also be used. The reaction is stirred until a clear solution is obtained. The solution is heated to 80° C. and the molten maleic derivative is added. The pH is kept between 6–8 during the reaction. The reaction is held at between 70° and 80° C. During that time the product becomes clear. The residual sulfite is checked by titration with iodine and becomes vanishingly small. The product is ready to use as prepared and may range in solids from 20% to 60% with 30–40% being the preferred concentration.

| Example Number | Maleate Derivative | | Sulfite | | Water |
|---|---|---|---|---|---|
| | Example | Grams | Type | Grams | Grams |
| 13 | 9 | 486.0 | $Na_2SO_3$ | 126.0 | 1530.0 |
| 14 | 10 | 501.0 | $Na_2SO_3$ | 126.0 | 1570.0 |
| 15 | 11 | 544.0 | $Na_2SO_3$ | 126.0 | 1675.0 |
| 16 | 12 | 1471.0 | $Na_2SO_3$ | 126.0 | 4000.0 |
| 17 | 9 | 486.0 | $K_2SO_3$ | 158.0 | 1610.0 |
| 18 | 10 | 501.0 | $K_2SO_3$ | 158.0 | 1650.0 |
| 19 | 11 | 544.0 | $K_2SO_3$ | 158.0 | 1755.0 |
| 20 | 12 | 1471.0 | $K_2SO_3$ | 158.0 | 4075.0 |

The products as prepared above are yellow liquids. They have very littie odor and a silky feel on the skin. In addition they are non-irritating to the eye and skin and non-comedogenic.

I claim:

1. A meadowfoam sulfosuccinate conforming to the following structure;

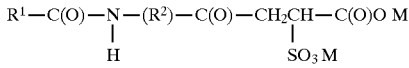

$R^1$ is derived from meadowfoam and is

60–65% by weight

12–20% by weight a mixture of

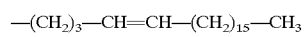

and

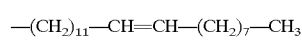

and

15–28% by weight $$-(CH_2)_3-CH=CH-(CH_2)_6-CH=CH-(CH_2)_6-CH_3;$$

$R^2$ is:

$$-(CH_2CH_2-O)_x-(CH_2CH(CH_3)O)_y-$$

x, and y are independentiy 0 or 1 with the proviso that x+y is greater than 0;

M is a cation selected from K or Na.

2. A meadowfoam sulfosuccinate of claim 1 wherein M is K.

3. A meadowfoam sulfosuccinate of claim 1 wherein M is Na.

4. A meadowfoam sulfosuccinate of claim 1 wherein x is 1, y is 0.

5. A meadowfoam sulfosuccinate of claim 1 wherein x is 0, y is 1.

6. A meadowfoam sulfosuccinate of claim 1 wherein x is 1, y is 1.

7. A meadowfoam maleate conforming to the following structure:

$$R^1(O)C-N(H)-(R^2)-C(O)-CH=CH-C(O)-OH$$

$R^1$ is derived from meadowfoam and is

60–65% by weight $$-(CH_2)_3-CH=CH-(CH_2)_{13}-CH_3$$

12–20% by weight a mixture of $$-(CH_2)_3-CH=CH-(CH_2)_{15}-CH_3$$

and $$-(CH_2)_{11}-CH=CH-(CH_2)_7-CH_3$$

and

15–28% by weight $$-(CH_2)_3-CH=CH-(CH_2)_6-CH=CH-(CH_2)_6-CH_3;$$

$R^2$ is $$-(CH_2CH_2-O)_x-(CH_2CH(CH_3)O)_y-;$$

x, and y are independentiy 0 or 1 with the proviso that x+y is greater than 0.

8. A meadowfoam maleate of claim 7 wherein x is 1, and y is 0.

9. A meadowfoam maleate of claim 7 wherein x is 0, and y is 1.

10. A meadowfoam maleate of claim 7 wherein x is 1, and y is 1.

* * * * *